(12) United States Patent
Raichman

(10) Patent No.: US 8,698,637 B2
(45) Date of Patent: Apr. 15, 2014

(54) MONITOR WORN BY USER FOR PROVIDING HYGIENE HABITS INDICATION

(75) Inventor: Yossef Raichman, Herzlia (IL)

(73) Assignee: Hyginex Inc., Los Angeles, CA (US)

( * ) Notice: Subject to any disclaimer, the term of this patent is extended or adjusted under 35 U.S.C. 154(b) by 519 days.

(21) Appl. No.: 13/061,954

(22) PCT Filed: Sep. 3, 2009

(86) PCT No.: PCT/IL2009/000854
§ 371 (c)(1),
(2), (4) Date: Mar. 3, 2011

(87) PCT Pub. No.: WO2010/026581
PCT Pub. Date: Mar. 11, 2010

(65) Prior Publication Data
US 2011/0169646 A1    Jul. 14, 2011

Related U.S. Application Data

(60) Provisional application No. 61/136,413, filed on Sep. 3, 2008.

(51) Int. Cl.
*G08B 21/00* (2006.01)

(52) U.S. Cl.
USPC ............... 340/573.1; 340/539.1; 340/541; 455/88; 422/119

(58) Field of Classification Search
USPC ............ 340/573, 539, 541, 639; 455/88; 422/119
See application file for complete search history.

(56) References Cited

U.S. PATENT DOCUMENTS

| | | | |
|---|---|---|---|
| 4,896,144 A | | 1/1990 | Bogstad |
| 5,812,059 A | * | 9/1998 | Shaw et al. ............... 340/573.1 |
| 2004/0090333 A1 | * | 5/2004 | Wildman et al. .......... 340/573.1 |
| 2006/0071799 A1 | * | 4/2006 | Verdiramo ................. 340/573.5 |
| 2008/0131332 A1 | * | 6/2008 | Nguyen et al. ................ 422/119 |
| 2008/0136649 A1 | * | 6/2008 | Van De Hey ............... 340/573.1 |
| 2009/0051545 A1 | * | 2/2009 | Koblasz ..................... 340/573.1 |

FOREIGN PATENT DOCUMENTS

| | | |
|---|---|---|
| EP | 1872802 | 1/2008 |
| GB | 2446871 | 8/2008 |
| JP | 06-292688 | 10/1994 |
| JP | 11-347107 | 12/1999 |
| JP | 2007-142835 | 6/2007 |
| JP | 2008-027436 | 2/2008 |
| WO | WO 02/21475 | 3/2002 |

(Continued)

OTHER PUBLICATIONS

Communication Relating to the Result of the Partial International Search Dated Feb. 8, 2010 From the International Searching Authority Re.: Application No. PCT/IL2009/000854.

(Continued)

*Primary Examiner* — Mohammad Ghayour
*Assistant Examiner* — Mark Rushing

(57) ABSTRACT

A method for analyzing hygiene habits of a user. The method comprises attaching a personal hygiene monitor to the user, using the attached personal hygiene monitor for detecting a plurality of personal hygiene events related to the user, logging the plurality of personal hygiene events to allow configuring a user hygiene profile of the user, and estimating a hygiene level of one or more hygiene habits of the user according to the user hygiene profile.

33 Claims, 4 Drawing Sheets

(56) References Cited

FOREIGN PATENT DOCUMENTS

| WO | WO 2007/001866 | 1/2007 |
|----|----------------|--------|
| WO | WO 2007/090470 | 8/2007 |
| WO | WO 2008/088424 | 7/2008 |
| WO | WO 2010/026581 | 3/2010 |

OTHER PUBLICATIONS

International Search Report and the Written Opinion Dated Mar. 26, 2010 From the International Searching Authority Re.: Application No. PCT/IL2009/000854.

International Preliminary Report on Patentability Dated Mar. 17, 2011 From the International Bureau of WIPO Re.: Application No. PCT/IL2009/000854.

Hama et al. "Hand-Hygiene Activity Classification With Accelerometers", IPSJ SIG TEchnical Reports 2008-CVIM-164, 2008(82): 239-244, Aug. 29, 2008. & Translation in English.

Translation of Notice of Reason for Rejection Dated Jul. 12, 2013 From the Japanese Patent Office Re. Application No. 2011-525677.

Hama et al. "Hand-Hygiene Activity Classification With Accelerometers", IPSJ SIG TEchnical Reports 2008-CVIM-164, 2008(82): 239-244, Aug. 29, 2008. Abstract in English.

\* cited by examiner

| Time | Event | Quality | Location |
|---|---|---|---|
| 00:08:21 28/07/2028 | Washing hands | 8/10 | Operating room 8 |
| 00:11:20 28/07/2028 | Wearing gloves | N/A | Operating room 4 |
| 00:11:40 28/07/2028 | Removing gloves | N/A | Operating room 4 |
| 00:11:45 28/07/2028 | Washing hands | 7/10 | Operating room 4 |
| 00:12:45 28/07/2028 | Washing hands | 7/10 | Dining room 1 |
| 00:13:45 28/07/2028 | Washing hands | 7/10 | Dining room 1 |
| 00:13:45 28/07/2028 | Spraying | 6/10 | Physiotherapy 1 |
| 00:13:50 28/07/2028 | Spraying | 6/10 | Patient bed 267 |
| 00:14:20 28/07/2028 | Wiping | 9/10 | Patient bed 268 |

FIG. 5

MONITOR WORN BY USER FOR PROVIDING HYGIENE HABITS INDICATION

RELATED APPLICATIONS

This application is a National Phase of PCT Patent Application No. PCT/IL2009/000854 having International filing date of Sept. 3, 2009, which claims the benefit of priority of U.S. Provisional Patent Application No. 61/136,413 filed on Sept. 3, 2008. The contents of the above applications are all incorporated herein by reference.

FIELD AND BACKGROUND OF THE INVENTION

The present invention, in some embodiments thereof, relates to a system and a method for monitoring hygiene compliance and, more particularly, but not exclusively, to a system and a method for monitoring personal hygiene compliance of users.

In various situations and environments, it is considered desirable to remind and/or to encourage people to perform personal hygiene tasks, such as washing their hands. Typical environments would include hospitals, care homes and hospices, where carers, such as nurses, doctors and therapists should wash their hands regularly, in particular when moving between treating different patients. Other environments where regular hand washing is required could include catering environments where food items are processed or at food processing facilities. It is necessary for people in such environments to take responsibility for their personal hygiene.

During the last years various devices have been developed in an attempt to improve the personal hygiene level of care takers and workers. This devices are designed to detects whether the user washes her hands or not and to output a sanitary signaling accordingly.

For example U.S. Pat. No. 5,952,924, filed on Dec. 4, 1997 describes a system for encouraging workers who work in a hygienically controlled area to wash their hands before exiting an associated sanitation area. Broadly, the present invention comprises a housing located in the sanitation area for receiving at least a portion of the hands of the worker. A detector is operatively associated with the housing. The detector detects whether or not the hands of the worker have recently been washed in response to the insertion of the hands of the worker into the housing. A communication media is also operatively associated with the detector for outputting one of a sanitary signaling media in response to the detection that the hands of the worker have been washed and an unsanitary signaling media in response to the detection that the hands of the worker have not been washed.

Another example is described in UK Patent Application No. GB 2417811A, filed on Aug. 12, 2005, that discloses hand washing detector device, suitable to be fitted to a person possibly on the hand or wrist, comprises a sensor for sensing a hand washing event and a timing module responsive to the sensor. The device may also include an alarm system wherein the timing module activates the alarm system when a first predetermined time limit is exceeded between hand washing events. The alarm may be audible, vibratory and/or visual and the sensor may detect the presence of water or any other chemical present during hand washing. The device may help in infection control by monitoring hand washing and reminding people to wash their hands regularly.

In addition, systems and methods for monitoring hygiene standards compliance in a certain environment have also been developed. For example, International Application No. PCT/EP2006/062895, filed on Jun. 2, 2006 describes a system and a method of monitoring hygiene standards compliance in a medical facility in which there is provided a surveillance network having a monitoring unit and a plurality of network units. There may additionally be provided a plurality of fixed network units. The monitoring unit, mobile network units and fixed network units are connected by way of a wireless personal area network (WPAN), in this case a ZigBee network. Identification signals are sent from the mobiles network units to the monitoring unit and the monitoring unit stores the identification signals in memory and generates a hygiene standards compliance profile for an individual associated with a particular mobile network unit. The hygiene compliance profile may provide information relating to the number of times that a particular individual washed their hands to information regarding the patients that that individual came into contact with over the course of a shift. Reports on the behavior of individuals or groups of individuals may be generated.

SUMMARY OF THE INVENTION

According to some embodiments of the present invention there is provided a method for analyzing hygiene habits of a user. The method comprises attaching a personal hygiene monitor to the user, using the attached personal hygiene monitor for detecting a plurality of personal hygiene events related to the user, logging the plurality of personal hygiene events to allow configuring a user hygiene profile of the use, and estimating a hygiene level of one or more hygiene habits of the user according to the user hygiene profile.

Optionally, the method further comprises generating an alarm when the hygiene level being beyond a predefined level.

Optionally, the method further comprises ranking the hygienic level of the user in relation to a plurality of users according to the hygiene level.

Optionally, the estimating is based on a schedule of the user.

Optionally, the logging comprises associating a time stamp with each the personal hygiene event, further comprising identifying at least one personal hygiene pattern according to respective the associated time stamps, the estimating being performed according to the at least one personal hygiene pattern.

Optionally, the using comprises using the attached personal hygiene monitor for gathering locational data regarding the user, further comprising identifying at least one personal hygiene pattern according to a combination of the locational data and at least one of the plurality of personal hygiene events, the estimating being performed according to the at least one personal hygiene pattern.

Optionally, the personal hygiene event is a member of a group consisting of: using a disposable tissue, washing hand action, taking shower action, replacing medical safety accessory action, replacing a pair of gloves action, and wearing a face mask action.

Optionally, the detecting and logging comprises detecting and logging the quality of the personal hygiene event, the estimating being performed according to respective qualities.

More optionally, the quality is estimated by measuring a member of a group consisting of: measuring the duration of the respective personal hygiene event, measuring the intensity of the respective personal hygiene event, measuring a concentration of at least one disinfecting agent involved in the personal hygiene event, measuring a presence of water during the personal hygiene event, measuring a humidity level during the personal hygiene event, measuring temperature during the personal hygiene event.

According to some embodiments of the present invention there is provided a wearable apparatus for analyzing hygiene habits of a user. The wearable apparatus, comprises at least one sensor configured for detecting a plurality of personal hygiene events, a repository configured for storing the plurality of personal hygiene events, an interface configured for forwarding the plurality of personal hygiene events to a remote analysis unit. The remote analysis unit is configured for estimating a hygiene level of at least one hygiene habit of the user according to the plurality of personal hygiene events.

Optionally, the wearable apparatus further comprises a wearing detector for detecting a wearing event of the wearable apparatus, wherein each the personal hygiene event is evaluated according to the wearing event.

Optionally, the at least one sensor comprises a plurality of sensors, each being configured for detecting a different of a plurality of physical stimulations, the at least one sensor being configured for detecting the plurality of personal hygiene events by combining the plurality of physical stimulations.

Optionally, the at least one sensor comprises a plurality of sensors, each being configured for detecting a different of a plurality of physical stimulations, the remote analysis unit being configured for estimating the hygiene level by combining the plurality of physical stimulations.

Optionally, the remote analysis unit maintaining a user hygiene profile documenting at least one hygiene habit related to the user, the remote analysis unit being configured for updating the user hygiene profile according to the plurality of personal hygiene events and calculating the hygiene level according to the user hygiene profile.

Optionally, the wearable apparatus is configured for receiving the hygiene level from the remote analysis unit, further comprising a hygiene indicator configured for presenting the hygiene level to the user.

Optionally, the at least one sensor comprises a hygrometer for detecting at least one of the plurality of personal hygiene events by measuring humidity in a proximity to the hands of the user.

Optionally, the at least one sensor comprises an alcohol sensor for detecting at least one of the plurality of personal hygiene events by measuring a concentration of alcohol vapours in a proximity to the user.

Optionally, the at least one sensor comprises an ultrasonic Doppler sensor for detecting at least one of the plurality of personal hygiene events by detecting running water by means of measuring Doppler Effect in a proximity to the user.

Optionally, the at least one sensor comprises an optical sensor for detecting at least one of the plurality of personal hygiene events by measuring a transparency of cleaning material in a proximity to the user.

Optionally, the at least one sensor comprises an acoustical sensor for detecting the sound of personal hygiene events by comparing between acoustical signals captured in a proximity to the user and a predefined audio pattern.

Optionally, the at least one sensor comprises a motion detection sensor for detecting a personal hygiene event by recording at least one gesture of the user and matching between the at least one gesture and at least one movement pattern of a personal hygiene event.

Optionally, the at least one sensor comprises an touch detector sensor configured for detecting a proximity of to a medical device and a processor configured for detecting a personal hygiene event according to the detected proximity.

Optionally, the at least one sensor is configured for detecting a hygiene protection event, the repository being configured for storing the hygiene protection event, and the interface being configured for forwarding the hygiene protection event to the remote analysis unit, the remote analysis unit being configured for estimating the hygiene level according to the hygiene protection event.

Optionally, the wearable apparatus further comprises a location detecting module configured for detecting a location of the user and logging it in the repository, the remote analysis unit being configured for estimating the hygiene level according to the location.

More optionally, the location is outside the boundaries of a building.

More optionally, the location is a member of a group consisting of: a include an operating room, a patient bed, a medical device, a physiotherapy room, a dining room, a kitchen, a production floor shop, food manufacturing area and a food manufacturing device.

According to some embodiments of the present invention there is provided a system for analyzing hygiene habits of a plurality of users. The system comprises a plurality of personal hygiene monitors each configured for being attached to a respective of the plurality of users to allow detecting and logging a plurality of personal hygiene events related thereto, and a hygiene analysis unit configured for managing a plurality of user hygiene profiles each documenting at least one hygiene habit of a respective of the plurality of users, the hygiene analysis unit being configured for receiving the plurality of personal hygiene events from a respective of the plurality of personal hygiene monitors and updating a respective of the plurality of user hygiene profile accordingly. The hygiene analysis unit is configured for calculating a hygiene level for each the user according to a respective of the plurality of user hygiene profiles.

Optionally, the system of further comprises a plurality of location detecting unit each configured for detecting the presence of at least one of the plurality of personal hygiene monitors in proximity thereto, wherein the hygiene analysis unit is configured for calculating the hygiene level according to detected presence.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 is an exemplary dataset of logged personal hygiene events, according to some embodiments of the present invention.

DESCRIPTION OF SPECIFIC EMBODIMENTS OF THE INVENTION

Figure 1:
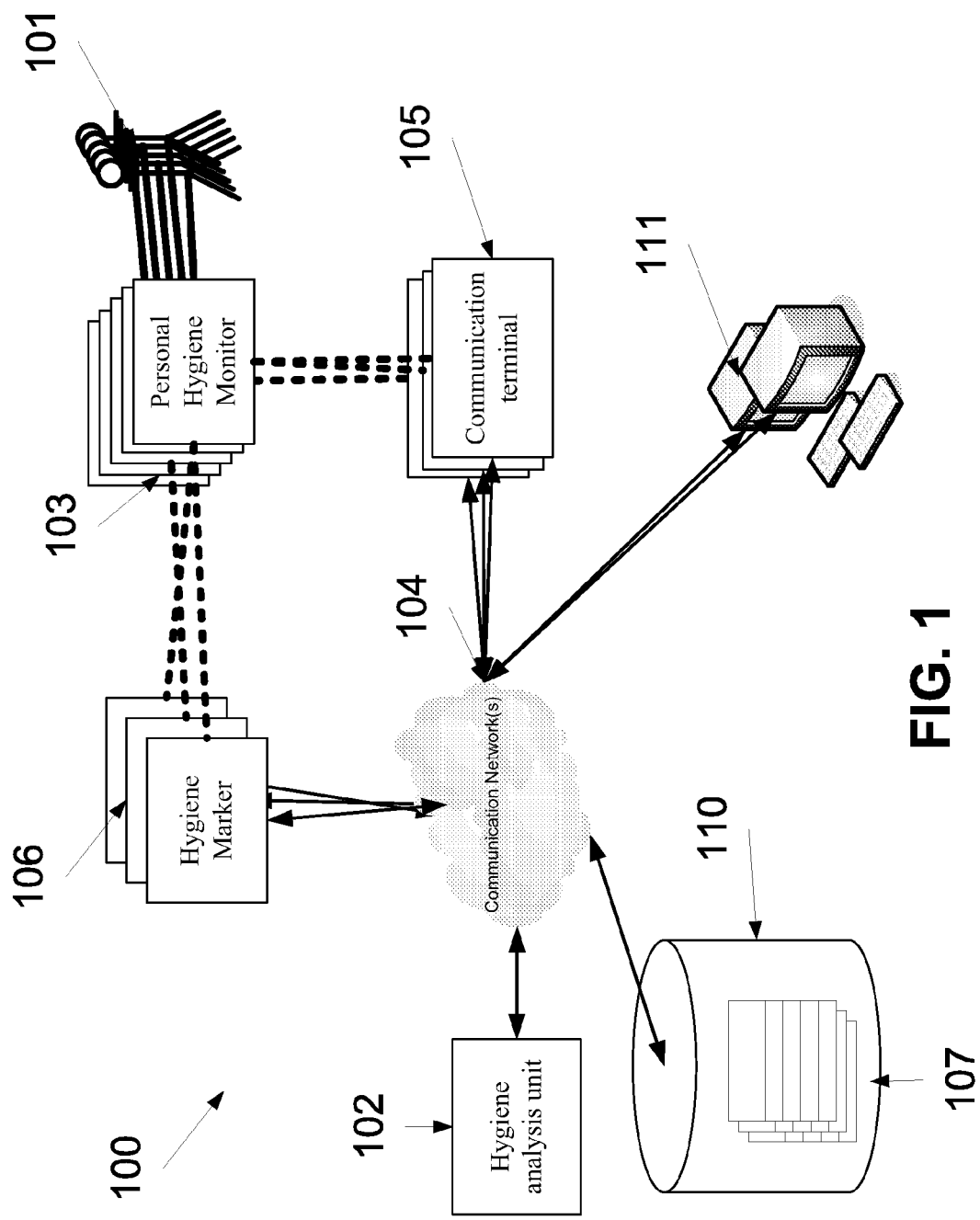
FIG. 1 is a schematic illustration of a system for analyzing hygiene habits of a plurality of users, according to some embodiments of the present invention.

The present invention, in some embodiments thereof, relates to a system and a method for monitoring hygiene compliance and, more particularly, but not exclusively, to a system and a method for monitoring personal hygiene compliance of users.

According to some embodiments of the present invention there are provided methods, systems, and apparatuses for monitoring hygiene habits and/or protocols of one or more users. Optionally, the monitoring is performed along a period of between few hours and several days, weeks, months, and/or years. Such embodiments allow ranking a plurality of users according to their compliance with hygiene protocols and/or habits in a certain area of interest, such as an institute, a facility, and/or a company, such as a hospital, a factory, a restaurant, a catering service and/or any other institute, facility, and/or company that enforce hygiene habits, as further described below.

According to some embodiments of the present invention there is provided a method for analyzing one or more hygiene habits of a user. The method is based on a personal hygiene monitor that is attached to the user, for example as a wristwatch, a bracelet, and/or a necklace. The personal hygiene monitor is used for detecting personal hygiene events, such as hand washing, showering, and replacing gloves, which are related to the user. The personal hygiene events are logged to allow the configuring a user hygiene profile of the user. Optionally, the personal hygiene events are logged on the personal hygiene monitor and transferred to a central analysis unit that hosts the user hygiene profile. As further described below, the central analysis unit may be accessed via a communication network, such as the internet. Now, after the personal hygiene events have been detected and logged, a hygiene level of one or more hygiene habits of the user is estimated according to the user hygiene profile. Optionally, the hygiene level is based on the frequency of personal hygiene events, the pattern of performing personal hygiene events, an/or on external data which has been gathered during, before, and/or after the performance of the personal hygiene events, such as timing and/or locational data.

According to some embodiments of the present invention there is provided a personal hygiene monitor with one or more personal hygiene sensors, such as a hygrometer, an alcohol sensor, an optical sensor, an acoustical sensor, motion detection sensor and a touch detector.

According to some embodiments of the present invention there is provided a system for monitoring and ranking a plurality of users according to their compliance with hygiene habits and/or protocols. Optionally, the system ranks the hygiene habits of each one of the users with respect to the hygiene habits of one or more of the other users. Optionally, the ranking of a certain user is expressed by the personal hygiene monitor of the user.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

System

Reference is now made to FIG. 1, which is a schematic illustration of a system 100 for analyzing hygiene habits of a plurality of users 101, according to some embodiments of the present invention. By analyzing personal hygiene levels of users, institutes such as hospitals, factories, and/or restaurants may enforce hygiene habits and/or improve their sanitary conditions, as further described below. For brevity, hygiene habits and/or protocols are referred to herein as hygiene habits.

The system 100 is based a hygiene analysis unit 102, which is optionally implemented on one or more servers, and a plurality of personal hygiene monitors 103.

The hygiene analysis unit 102 and the plurality of personal hygiene monitors 103 communicate, optionally via one or more communication terminals 105 which are connected to a communication network 104, such as a wired network, for example a local area network (LAN) and wide area network (WAN), or a wireless network, for example as a wireless LAN (WLAN) and/or wireless personal area network (WPAN). The hygiene analysis unit 102 optionally communicates with one or more client terminals 111. As used herein a client terminal means a personal computer, a thin client, a personal digital assistant (PDA), and a Smartphone. Optionally, the personal hygiene monitor 103 or any component thereof is integrated into a client terminal.

The communication terminals 105 interfaces with the plurality of personal hygiene monitors 103 in a wirelessly or via a wired connection, for example as further described below. Optionally, the system 100 comprises one or more hygiene markers, for example as described below.

In some embodiments of the present invention, the hygiene analysis unit 102 manages a plurality of user profiles 107. Each user profile 107 logs personal hygiene events which are related to a certain user, such as a caregiver, for example a nurse, a physician, a paramedic, a therapist, and a member of the emergency medical service, a food processing facility employee, a catering employee, for example a cook, a food delivery employee, and a waiter. As used herein, a personal hygiene event means any event that has an effect on the hygienic level of a user. Such personal hygiene event may be hygienic habits like using disposable tissues, washing hands, disinfecting hands using a disinfect agent, such as alcohol, taking showers, replacing medical safety accessories, such as latex gloves, wearing a face mask, such as a surgical mask, being in a hygiene event related location, such as a shower, a proximity to sink, and/or a disinfecting agent dispenser, and the like.

Optionally, each user profile 107 is associated with a user identifier (ID), a list that documents the personal hygiene events, which are related to the user, and a current hygiene score that reflects an estimated evaluation of the hygiene habits of the user, optionally calculated as described below. The user profiles 107 are designed to store logged personal hygiene events which are related to the user.

Monitor

Figure 2:
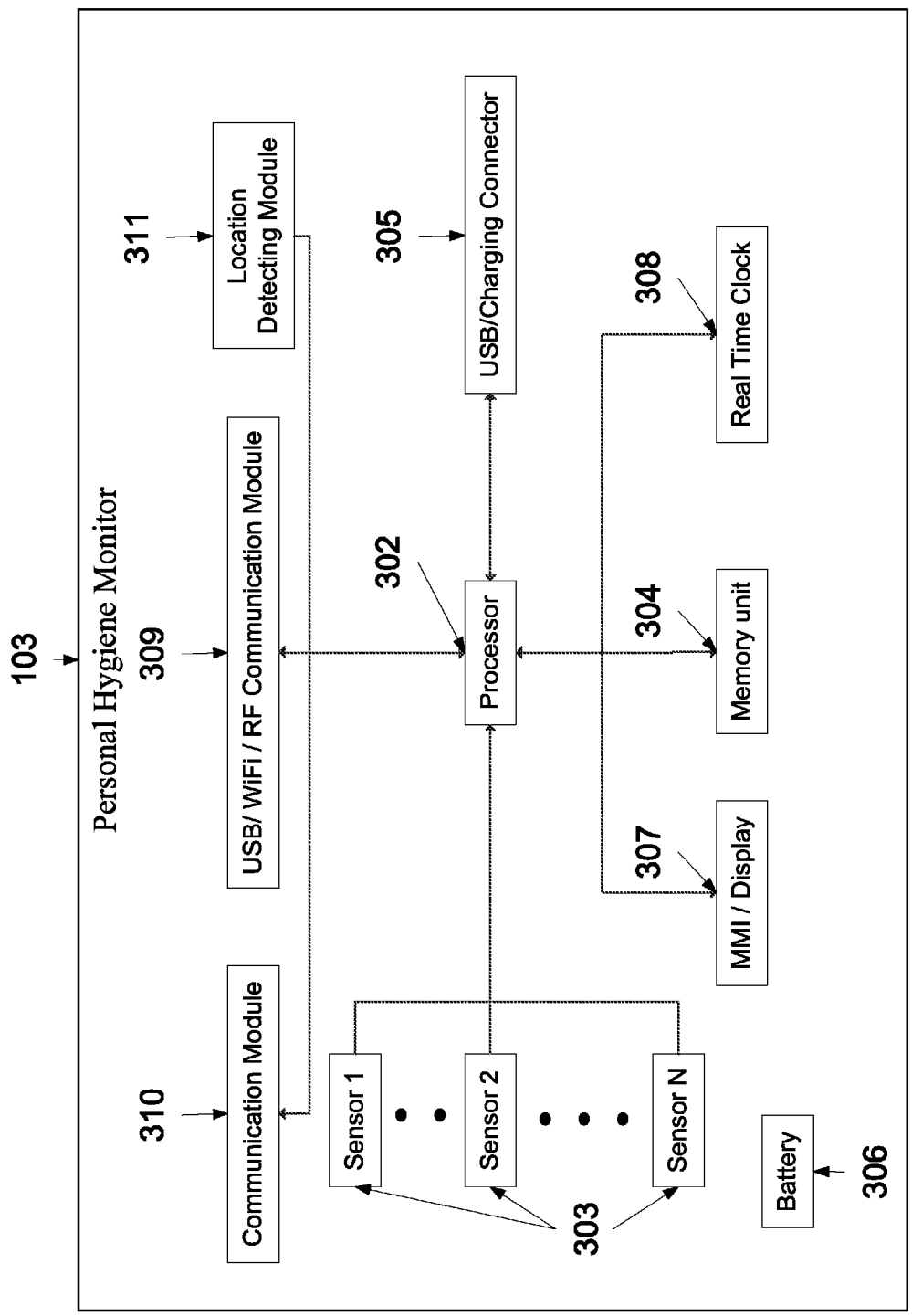
FIG. 2 is a schematic illustration of exemplary components of an exemplary personal hygiene monitor, according to some embodiments of the present invention.
Figure 3:
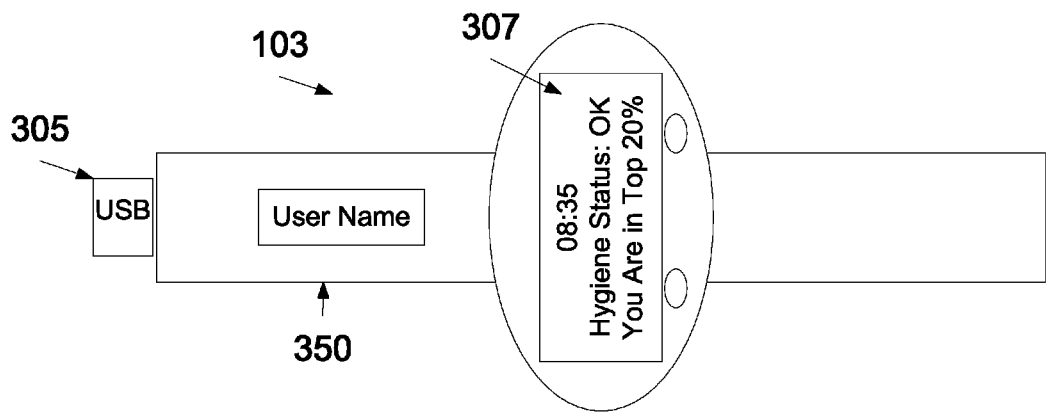
FIG. 3 is a schematic illustration of an armlet that is designed to host the components of the personal hygiene monitor, according to some embodiments of the present invention.

Reference is now made to FIG. 2, which is a schematic illustration of exemplary components 300 of an exemplary personal hygiene monitor 103, according to some embodiments of the present invention. Reference is also made to FIG. 3, which is a schematic illustration of an armlet or a wristwatch 350 that is designed to host the components of the personal hygiene monitor 103, according to some embodiments of the present invention. It should be noted that the personal hygiene monitor 103 may be integrated in any wearable device, such as a ring, a badge, a necklace a band or any wearable device that is designed to be attached to the user while she performs duties which require relatively high level of hygiene. For example, if the user is a medical carer, such as a physician, the personal hygiene monitor 103 is designed to be attached to her while she performs duties, such as treating patients, either in a hygiene monitored environment, such as hospital, or outside the hygiene monitored environment, for example while the physician is performs a duty as part of an emergency medical service that provides medical services outside the hygiene monitored environment.

In some embodiments of the present invention, the personal hygiene monitor 103 includes a wearing detector for detecting whether the user actually wears the personal hygiene monitor 103 in a certain point in time or not. The wearing detector is optionally a button that is pressed during the wearing of the personal hygiene monitor 103, for example during the locking of a respective armlet around the hand of the user. In such a manner, the personal hygiene monitor may either be activated and/or change an operation mode whenever the user wears the personal hygiene monitor. Such a wearing detection is important in order to accurately documenting and attributing the receptions and/or the absence of receptions from the one or more hygiene event sensors which are outlined above and described below. For example, absence of receptions from the one or more hygiene event sensors may be documented as either a period during which the user did not performed and/or participate in a personal hygiene event if the wearing detector detected the wearing of the personal hygiene monitor 103 or as a null period if the wearing detector did not detect the wearing of the personal hygiene monitor 103. For clarity, a null period is a period during which the hygienic habits of the user are not documented.

In some embodiments of the present invention, the personal hygiene monitor 103 includes a processor 302, such as a microcontroller, which is connected to a memory unit 304, such as a flash memory and one or more hygiene event sensors 303.

The one or more hygiene event sensors 303 are designed to detect, separately and/or in combination, a personal hygiene event. For example, a personal hygiene event may be detected if only one of the hygiene event sensors 303 detects a personal hygiene event above a predefined value, for example as further described below, or if a sum, a mean, and/or an average value of the readings made by the hygiene event sensors 303 is above a predefined threshold. Each one of the hygiene event sensors 303 is designed for detecting a personal hygiene event according to a physical stimulus and/or a set of physical stimulations, such as thermal energy, electromagnetic energy, acoustic energy, pressure, magnetism, and/or motion and producing a signal, usually electrical for indicating this detection and/or optionally the quality of this detection, for example as described below.

Optionally, one of the hygiene event sensors 303 is a chemical detector, such as an Ion mobility spectrometer (IMS), for detecting and identifying concentrations of chemicals which are related to detergents in a proximity to the hands of the user. Such a chemical detector may be used for sensing the presence of water and/or any chemical that is present during a hand washing action. The chemicals may be detected in the water and/or during personal hygiene events, such as spraying the hands with a spray, such as a gel spray, using disinfecting agent, such as alcohol, using a disposable wipe for washing the hands, and the like. Optionally, one of the hygiene event sensors 303 is a hygrometer for measuring humidity. The hygrometer may be defined to measure the humidity in a proximity to the hands of the user, thereby to determine whether the user is washing her hands or not. Additionally or alternatively the hygrometer may include a capacitive sensor for detecting moisture. Additionally or alternatively, the hygrometer may be used for detecting the wearing and/or the replacing of gloves. The hygrometer senses a change in the humidity that surrounds it while gloves are worn and/or worn down by the user and logs a personal hygiene event accordingly.

Optionally, one of the hygiene event sensors 303 is a conductivity sensor for measuring conductivity of a fluid in a proximity to the hands of the user and/or the personal hygiene monitor 103. Optionally, the conductivity sensor detects properties of water, gel, and/or disinfecting material by use of resistive, capacitive, and/or inductive methods. Such sensors may be used for determining whether the user is washing her hands or not and/or the quality of a personal hygiene event by estimating the composition of the water, gel, and/or disinfecting material which is used during the personal hygiene event.

Optionally, one of the hygiene event sensors 303 is an alcohol sensor configured for detecting the presence and/or concentration of alcohol vapours. Optionally, the alcohol sensor is mounted to enable the detection of personal hygiene events such as hand washing with alcohol, alcohol based gels and the like. For example, see the datasheet of Futurlec™ alcohol sensors, which is incorporated herein by reference.

Optionally, one of the hygiene event sensors 303 is an acoustical sensor that is configured for detecting the sound of personal hygiene events. Optionally, the acoustical sensor is associated with one or more predefined audio patterns of personal hygiene events, such as running water, a hand washing action, and a spraying.

Optionally, one of the hygiene event sensors 303 is an ultrasonic Doppler sensor for detecting running water by measuring Doppler Effect.

Optionally, one of the hygiene event sensors 303 is a motion detection sensor, such as an accelerometer and a gyroscope, which monitors the motion of the personal hygiene monitor 103 to detect personal hygiene motion patterns. Such a monitoring allows tracking gestures of the user and comparing them with one or more movement patterns each defines gestures taken during a respective personal hygiene event, such as washing hands or replacing a robe and/or a pair of gloves.

In such an embodiment, the motion detection sensor may be associated with one or more movement patterns each indicate a personal hygiene event. For example, the shacking of the hands in a hand washing pattern may be recorded as a personal hygiene event. Optionally, the patterns are recorded in advance in a configuration stage which is performed by the user.

Optionally, one of the hygiene event sensors 303 is a touch detector sensor. Such a sensor may be used for detecting a touching event during which the user touches a patient, a medical tool and/or any other person or a device. The touch detector sensor may include a magnetic sensor that detects fluctuations in a small magnetic, optionally electromagnetic, field in proximity thereof. Such a change may indicate that the user touches an element and/or a user that causes the fluctuations. When a user touches, with her bare hands, an element, a person, and/or an animal, the sterility of the user's hands decreases. The touch detector may detect the fluctuations in a magnetic field that optionally surrounds the hygiene event sensors 303 and registering the touching event in the memory of the personal hygiene monitor 103. Optionally, the touch detector identifies the time during which the user touched an element according to the touch pattern of the detected fluctuations. Optionally, touch detector tracks the amplitudes of the electronic field which vary when the user's body is moved toward the element, when the user's body is moved away from the element and/or when the user remain constant while touching the element. In such manner, the touch detector may change the quality of the detection event according to the time the user touched the element and/or according to a match with different touching patterns each indicative of a different touched element, such as a body of patient. a tap, a towel, a keyboard, and the like.

Such an event is optionally logged in the memory unit 304 of the personal hygiene monitor 103 and calculated, during the analysis of the hygienic level of the user, as an event that reduces the hygiene level of one or more hygiene habits of user, for example if it is not followed by a respective personal hygiene event, such as a hand washing action.

Optionally, one of the hygiene event sensors 303 is a proximity sensor that is used for detecting the proximity of hygiene related devices. For example, the proximity sensor may include a magnetic sensor that estimates the distance between the device and a tap or a disinfectant dispenser, such as a soap dispenser. Optionally, the proximity sensor senses the alternating magnetic field of the running water and determines the quality of the personal hygiene event accordingly. Optionally, the hygiene related devices are installed with a personal hygiene event indicator that is designed to transmit a personal hygiene event indication in response to the activation thereof. For example such an indicator may be connected to a detergent dispenser, such as a soap or detergent dispenser.

In such a manner the indicator transmit an indication which is intercepted by the personal hygiene monitor 103 that logs a respective personal hygiene event accordingly. Optionally, the personal hygiene monitor 103 includes communication module 310 that allows the intercepting of these indications.

Optionally, the proximity sensor is designed to sense the intensity of a transmitter, such as a wireless application protocol (WAP) gateway or switch. In such an embodiment, the detected intensity, which is optionally logged, may be used for determining the geographical location of the personal hygiene monitor 103.

Optionally, the touch detector sensor is designed to sense a hygiene protection event, such as a wearing gloves event. In such an embodiment the touch detector sensor may include a pressure sensor that senses the pressure that is applied by the gloves. The touch detector sensor may include optical sensor for detecting the presence of an article for longer then a predefined period.

Optionally, one of the hygiene event sensors 303 is a humidity sensor which is configured to detect the presence of the user in a humid location, such as a shower.

Optionally, one of the hygiene event sensors 303 is an optical sensor, such as a lucidity sensor for measuring the transparency of water, gel, and/or any other liquid that is used for cleaning the hands of the user. Optionally, the optical sensor is an active sensor that is used for emitting light having predefined properties and detecting different characteristics of the liquid and/or gel by measuring the polarization and/or the reflection of the emitted light.

Optionally, the hygiene event sensors 303 are designed for providing a relative value that represents the quality of the personal hygiene event. For example, the quality of the events which are detected by a chemical sensor may be based on the detected concentration of chemicals. The quality of the events which are detected by a hygrometer may be based on the level of the measured moisture, the time during which water flows in the proximity of the hygiene event sensors 303, the time and/or intensity of the hand washing, the concentration of detected disinfecting agents, and the like. Optionally, the hygiene event sensors 303 include a thermometer for measuring temperature during a personal hygiene event. Optionally, the thermometer is used for determining the temperature of water used in a personal hygiene event, such as hand washing, and ranking the quality of the personal hygiene event accordingly.

As described above, the personal hygiene monitor 103 may use a plurality of hygiene event sensors 303. Optionally the quality of the events which are detected by the hygiene event sensors 303 may be based on a cumulative value that is calculated by combining data from some or all the hygiene event sensors 303. For example, a sum, a mean, and/or an average of the qualities which has been given to a certain hygiene event by a plurality of hygiene event sensors 303 may be used for determining the quality of an event.

In use, the one or more hygiene event sensors 303 detect personal hygiene events, for example as described above. The processor 302 logs the identified hygiene events in the memory unit 300. Optionally, each hygiene event is tagged with a time stamp that reflects the time, or the approximate time, in which the relevant hygiene event has been identified. The time stamp may be based on the clock of the processor and/or on an external clock, such as a real time clock (RTC) 308. As used herein, real time means within less than 10 seconds, for example less than 1 second, 0.5 second, 0.1 second and the like.

Optionally, the personal hygiene monitor 103 includes a location detecting module 311 for identifying the location of the user during a personal hygiene event. Optionally, the location detecting module 311 comprises a global positioning system (GPS) module to allow identifying the exact location of the user in open spaces, such as a field hospital and a vicinity to an ambulance. Optionally, the location detecting module 311 comprises a tag reader, such as a radio frequency identification (RFID) reader for identifying the presence of tags, such as RFID tags. In such an embodiment, the location detecting module 311 may be used for detecting the presence of RFID tags in the proximity thereof. Optionally, areas of interest in a medical center, such as a hospital, are tagged in a manner that allows the personal hygiene monitor 103 to identify the location of the associated user. Such areas of interest may include an operating room, a patient bed, a medical device, a physiotherapy room, a dining room, a kitchen, a production floor shop, and a food manufacturing device and/or area.

In use, the location detecting module 311 may log information about the location of the user, optionally with association to a respective time stamp, which is optionally taken from the RTC 308. For instance, FIG. 5 depicts an exemplary dataset of logged personal hygiene events. Each personal hygiene event is time and location tagged. Optionally, the quality of the personal hygiene event is documented when available.

Optionally, the system comprises a plurality of hygiene markers 106 each designed to detect the presence one or more of the personal hygiene monitors 103 in proximity thereto. Optionally, each hygiene marker 106 is associated with and optionally placed in proximity to or in a certain area of interest, such as a patient bed, an operating room, a tap, a food processing device, and/or a dining room. Optionally, each hygiene marker 106 includes an RFID reader for reading the ID information which is stored in an RFID tag that is installed in the personal hygiene monitors 103 which are located in the proximity thereto. The data about the presence of the personal hygiene monitors 103 is forwarded to the hygiene analysis unit 102 that uses it as locational information when identifying personal hygiene patterns. Optionally, each detected presence is time stamped.

According to some embodiments of the present invention, the personal hygiene monitor 103 reacts to the detection of a personal hygiene monitor. Optionally, the reaction is determined according to the hygiene level of the user. For example, if the hygiene level is below a certain threshold, the personal hygiene monitor 103, which optionally includes a presentation unit, such as a speaker, a display, and/or one pr more lights, presents an alarm that is indicative of a low hygiene level, for example sounds a "please wash your hand" announcement, displays a red light blinking and the like. If the hygiene level is above a certain threshold, the personal hygiene monitor 103 presents a notification that is indicative of a high hygiene level, for example sounds a "clean" announcement, displays a green light and the like. In such an embodiment, the personal hygiene monitor 103 may be attached to a tap and indicate the user that she has to wash her hands and/or attached to an entrance of an operation room and indicate the user that she has to replace gloves.

Optionally, the personal hygiene monitor 103 notifies the user when there is a change in her hygiene level that occurs as an outcome of an action performed with a hygiene device that is associated therewith. For example, when a user with low hygiene level washes her hands and the sensors of the personal hygiene monitor 103 triggers an increase in her low hygiene level, the personal hygiene monitor 103 presents a notification that rewards the user and/or notify her about the status change.

According to some embodiments of the present invention, the personal hygiene monitor 103 includes a quantity sensor. As described above, the personal hygiene monitor 103 may be attached to a detergent dispenser, such as a soap dispenser and/or detergent dispenser. In such an embodiment, the personal hygiene monitor 103 may be used for verifying that the amount of soap and/or detergent which are released in a personal hygiene event, such as washing hands, is sufficient for increasing the hygiene level of the user. Optionally, the quantity sensor includes a scale for measuring the weight of the soap and/or the detergent in the dispenser. Optionally, the quantity sensor includes an optical sensor, for example as described above, for estimating a change in the amount of the soap and/or the detergent. It should be noted that any sensor which may be used for detecting an amount change may be used as a quantity sensor.

In such a manner, a detection of a change in the weight and/or in the amount of the soap and/or the detergent, which is indicative of a dispensing of a sufficient amount of soap and/or detergents, is considered as a personal hygiene event. On the other hand, a change, which is indicative of an insufficient amount of soap and/or detergents, is considered as a failure to perform a personal hygiene event.

Optionally, the processor 302 is connected to a memory card reader that reads content stored in memory cards. The memory cards are optionally solid-state electronic flash memory data storage devices such as CompactFlash™ cards, SmartMedia™ cards, Memory Stick™ cards, Secure Digital™ cards, miniSD™ cards, or MicroSD™ cards. In such an embodiment, the memory unit may be based on the memory card reader and the logging of the personal hygiene events may be performed on a memory card.

Optionally, the processor 302 is connected to a data interface 305 for forwarding the data which is logged in the memory unit. Optionally, the data interface 305 is based on wired connection, for example a universal serial bus (USB) interface. Alternatively or additionally, the processor 302 is connected to a wireless data interface 309, such as an example an infrared (IR) interface, a wireless fidelity (Wi-Fi) interface, a Bluetooth™ module, and the like.

The processor 302 is connected to a power source 306, optionally via a management integrated circuit (IC) that contains battery charging and control circuitries for managing the power source. Optionally, the power management IC 104 is connected to built-in battery housing with rechargeable batteries that provides the needed power. Optionally, one or more lithium polymer (Li-Po) rechargeable cells or batteries. The USB connection 305 may be used for charging the cells or batteries. Optionally, the batteries are charged by any external and/or internal charging element that converts the user's motion to energy, such as a kinetic charger.

Optionally, the personal hygiene monitor 103 includes a local personal hygiene manager for generating alarms and/or hygiene indications according to the logged personal hygiene events. In such an embodiment, the manager may monitor the logged data and matches it with one or more predefined personal hygiene patterns, which are defined as described below. For example, the personal hygiene monitor 103 may be used for generating a personal hygiene indication in response to the lack of personal hygiene events along a predefined period or in response to the detection of a personal hygiene pattern, such as the presence of the user in an area of interest, such as an operating room, without the detection of a personal hygiene event in a certain quality during a predefined period.

Optionally, the personal hygiene monitor 103 includes an exemplary man-machine interface (MMI) 307 that is optionally connected to the local personal hygiene manager. The MMI 307 optionally comprises a display, such as a liquid crystal display (LCD) display, for presenting one or more user indications, such as the aforementioned alarms and/or hygiene indications of the manager. FIG. 3 displays an exemplary display 307 which is position in a wristwatch.

The MMI 307 may comprise an input device, such as a keypad for allowing the user to enter data and/or to select operation modes. Optionally, the MMI includes one or more speakers for generating audible indications. Optionally, the MMI includes one or more vibrating unit for generating tactile indications. As further described below, the MMI 307 may display the hygiene level of one or more hygiene habits of user. Optionally, the MMI 307 is designed for displaying indications and/or alarms according to the measurements of the sensors, for example according to the outputs of the personal hygiene monitor 103.

Optionally, the personal hygiene indication is based on the quality of the related measurements. For example, the MMI 307 may includes one or more light emitting diodes (LEDs) which are designed to be activated according to the quality of a hand washing event. A red LED is activated in response to insufficient quality, for instance a reading of low moisture, a yellow LED is activated in response to sufficient quality, for instance a reading of average moisture level, and a green LED is activated in response to a good quality, for instance a reading of high moisture level. In such an embodiment, the personal hygiene monitor 103 provides the user with an immediate indication the quality of the personal hygiene event.

Methods and Analysis

Figure 4:
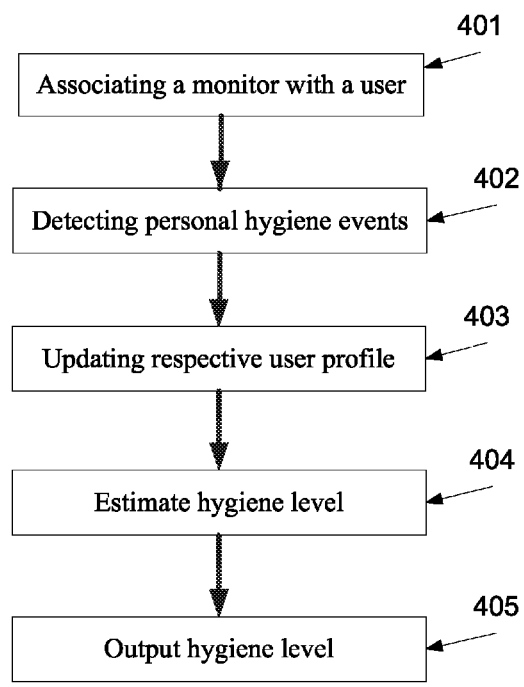
FIG. 4 is a flowchart of a method for analyzing a hygiene level of a user, according to some embodiments of the present invention.

Reference is now also made to FIG. 4, which is a flowchart 400 of a method for analyzing a hygiene level of a user, according to some embodiments of the present invention. Though the method that is described in FIG. 3 depicts a process of analyzing a hygiene level of a single user, it may be implemented simultaneously by any number of personal hygiene monitor 103, for example the personal hygiene monitors 103 of the system which is depicted in FIG. 1. For clarity, the system 100 may be used for analyzing any number of users.

First, as shown at 401, the user is associated with a personal hygiene monitor. In an exemplary embodiment of the present invention, the personal hygiene monitor 103 is inserted in a bracelet or a watch, for example as shown at FIG. 3, which is attached to the user. The ID tag of the personal hygiene monitor 103 is adjusted to represent the user and optionally to match the ID that is associated with a respective user profile that is managed by the hygiene analysis unit. Optionally, the ID is stored in the memory unit 304 of the personal hygiene monitor 103 and associated with the stored logged records. Now, as shown at 402, the personal hygiene monitor 103 is used for detecting one or more personal hygiene events which are related to the user. As described above, one or more hygiene event sensors 303 may be used for detecting personal hygiene events.

Now, as shown at 403, the personal hygiene monitor 103 is used for updating the respective user hygiene profile 107 of the user. As described above, the system 100 may include one or more communication terminals 105. Periodically and/or randomly the user establishes a user profile update session with the hygiene analysis unit 102 via one of the communication terminals 105. During the session, the personal hygiene monitor 103 updates the respective user hygiene profile 107 of the user. Optionally, each communication terminal 105 has a data input interface, such as a wired connecter, for example a USB connector and/or a wireless connector, such as an IR reader, for communicating with the personal hygiene monitor 103. An exemplary connection may be established when the user connects the USB connector 305 to the USB interface of one of the communication terminals 105. In another embodiment of the present invention, the connection is performed wirelessly and established whenever the wireless interface of the communication terminal 105 detects the presences of the personal hygiene monitor 103 in proximity thereto. The connection allows the personal hygiene monitor 103 to forward the logged personal hygiene events to the hygiene analysis unit 102 that updates, accordingly, the user profile that documents the hygiene habits of the user.

Now, as shown at 404, the hygiene level of one or more hygiene habits of user is estimated according to the user hygiene profile. The estimation may be done periodically, randomly and/or according to triggering events such as user requests and established connections with personal hygiene monitors 103. Optionally, as shown at 405, the estimated hygiene level is outputted. Optionally, the estimated hygiene level is forwarded the respective personal hygiene monitor 103, allowing the presentation thereof to the user, for example by the MMI 307. The forwarding is optionally performed as part of the user profile update session. In such an embodiment, the user forwards the logged records to the hygiene analysis unit 102 that provides, in response, optionally via the communication terminal, the hygiene level of the respective user. As further described below the estimated hygiene level may be relative to the hygiene level of other users, for instance as depicted in FIG. 3, or absolute.

Based on the logged personal hygiene events, the hygiene analysis unit 102 may perform an analysis of the hygiene habits of the user. The analysis may be a based on statistical analysis of a history of recorded personal hygiene events. Additionally or alternatively, the analysis may be a based on a comparison, optionally statistical, of recorded personal hygiene events of other users. In such an embodiment, the hygiene level that is given to the user may depend on the performances of other users and may be changed dynamically accordingly.

Optionally, the hygiene analysis unit 102 takes into account the time during which the personal hygiene events have been recorded and/or the frequency of the personal hygiene events. In such an embodiment, personal hygiene events which have been logged or missing after the working hours does not affect the hygiene level of one or more hygiene habits of user. Optionally, the hygiene analysis unit 102 is configured for generating a hygiene level that reflects the user habits during the working hours and another hygiene level that reflects the user habits after the working hours. In such a manner, the user may receive indication of her hygiene level in any part of her daily routine. Optionally, the hygiene level that reflects the user hygiene habits after the working hours is used as a reference value for evaluating her sterility level when she starts working.

Optionally, the hygiene analysis unit 102 uses one or more predefined personal hygiene patterns for scoring the hygiene level of one or more hygiene habits of user. For example, a predefined personal hygiene pattern may define a preferred period between personal hygiene events, and a preferred period between personal hygiene events of a certain kind.

In some embodiments of the present invention, each predefined personal hygiene pattern defines a certain hygiene habit, for example as a pattern of personal hygiene events along a timeline or the occurrence of a personal hygiene events before, during, and/or after a hygiene sensitive operation, such as treating a patient or preparing a food product. In such an embodiment, the aforementioned sensors may be used for detecting and logging events which are indicative on a hygiene sensitive action, such as entering an area of interest, touching a person and/or a medical device, and the like. As described above, the personal hygiene monitor 103 may comprise a location detecting module 311 for identifying the location of the user. When the personal hygiene monitor 103 detects a personal hygiene event it associates it with the identified location of the user. Optionally, the personal hygiene monitor 103 records the location of the user periodically, constantly, and/or randomly. Such a log can be used to determine whether, which, and to what extent a personal hygiene event has occurred, or repetitively occurred, while the user spends time in a certain area.

Optionally, the predefined personal hygiene pattern defines associations between locations and personal hygiene events. For example, the predefined personal hygiene pattern may define that in a personal hygiene event, such as hand washing action, occurs a predefined period before the entrance of the user to a certain area of interest, such as an operating room. In another example, the pattern defines that the presence of the user in an area of interest occurs in parallel to a predefined number of personal hygiene events. As described above, the system 100 may communicate with one or more hygiene markers 106 which are designed for detecting the presence of the personal hygiene monitor 103 in a certain area of interest. Optionally, the hygiene analysis unit 102 receives the locational data from the hygiene markers 106 and uses it for detecting a match to a location based pattern. Optionally, the hygiene level of one or more hygiene habits of user is determined according to a match between the information logged in the personal hygiene monitor 103 and the predefined personal hygiene patterns. Identifying such a match indicates that the user is following hygiene habits which are defined by the matching predefined personal hygiene patterns and therefore increases the hygiene level of one or more hygiene habits of user.

As described above and depicted in FIG. 5, each personal hygiene event may be logged with a quality tag that represents the quality thereof. In such an embodiment, the contribution of each personal hygiene event or pattern may be weighted according to a respective quality tag.

Optionally, the hygiene analysis unit 102 grades the hygiene level of one or more hygiene habits of user on a scale, such as spotless, very clean, clean, semi clean, not clean, and contaminated apprehension.

In some embodiments of the present invention, as shown at 405, the hygiene analysis unit 102 forwards the hygiene level back to the respective personal hygiene monitor 103, to a central hygiene analysis unit, and/or to one or more client terminals 111, such as the client terminal 111 of the user and/or the client terminal 111 of her supervisor. Optionally, the hygiene level is time tagged and logged in a repository 110 that is connected to the hygiene analysis unit 102, optionally via the communication network 104.

In some embodiments of the present invention, the hygiene analysis unit 102 is designed to yield one or more hygiene reports according to one or more user hygiene profiles 107 which are optionally stored in the repository 110. The hygiene report may present the hygiene level of one or more hygiene habits of user in relation to the hygiene level of other users. For example, the report may show the percentile in which the hygiene level of one or more hygiene habits of user is in relation to the hygiene level of other users. In such an embodiment, the system 100 may be used to identify who are the users with the worst and/or the best hygiene levels. As described above, the hygiene analysis unit 102 may be accessed by remote client terminals 111, allowing remote users, such as administrators and managers to issue the aforementioned reports and/or to search for current information that is related to certain users. Optionally, the hygiene analysis unit 102 is connected to a web server that hosts a designated website that allows access thereto.

Optionally, hygiene analysis unit 102 is designed to generate alarms whenever the hygiene level of one or more users is below a predefined level. Such an alarm may be sent to their personal hygiene monitors 103 and/or to one or more client terminals 111, for example by an email. For example, if the hygiene level of a certain user is below a predefined level the hygiene analysis unit 102 forwards an alarm to the respective personal hygiene monitor 103 that uses the MMI 307 for presenting the alarm, for example as a tactile, visual, and/or audible indication. In another example, the alarm is sent to a client terminal 111 that is associated with the user, her supervisor, and/or an administrator that supervises on the hygiene habits of the plurality of users.

In some embodiments of the present invention, the personal hygiene monitor 103 includes a hygiene analysis module, such as the aforementioned manager. The hygiene analysis module is designed to locally analyze the logged records in the memory unit and to output a hygiene level of one or more hygiene habits of user accordingly. In such an embodiment, the hygiene analysis module may generate an alarm when the hygiene level is below a predefined range and forward the alarm for presentation by the MMI. Optionally, the user uses a client terminal 111 for accessing her user profile and/or for generating a report.

Workers Management

In some embodiments of the present invention, the hygiene analysis unit 102 is designed to monitor the location of users, such as care takers and workers, in a certain area of interest. In such an embodiment, the logged personal hygiene events may be considered as presence indications, allowing real time monitoring pertaining to the geographic location of the user in the area of interest and/or the presence of the user in the area of interest. In such embodiments, the hygiene markers 106 may be configured to gather data about any personal hygiene monitor 103 that is detected in there perimeter and forward the gathered data to the hygiene analysis unit 102, for example as described above. Additionally or alternately, presence markers (not shown) are added to the system 100, allowing a full or a partial coverage of the area of interest. Optionally, the hygiene analysis unit 102 is designed to issue and/or present a report specifying the geographic location of the workers.

According to some embodiments of the present invention, the hygiene analysis unit 102 parallelly gather data pertaining to location and/or presence of the users and pertaining to the there hygiene level, for example as described above. In such an embodiment, the hygiene level of a worker during the time she spent in work may be monitored and optionally rated. Optionally, the hygiene analysis unit 102 receives presence data about punched in and/or punched out users from an external presence system. The arrival and departure times are used as anchors for the hygiene pattern calculations.

Optionally, the external presence system updates the hygiene analysis unit 102 with the actual working schedule of the users. In such an embodiment, a user profile may be adjusted according to a working schedule.

Optionally, the analysis unit 102 is connected to barriers, such as automatic doors and turnstiles. In such an embodiment, hygiene marker 106 may be associated with and/or placed in proximity to a barrier. The hygiene marker 106 identifies personal hygiene monitors 103 which are placed in proximity to the barrier, for example 2 meters or less therefrom and forwards the detection data to the analysis unit 102. The analysis unit 102 computes the hygiene levels and/or hygiene related events of the user that is associated with the personal hygiene monitors 103 and accordingly instructs the opening and/or closing of the barriers. For example, the detection of a personal hygiene monitor 103 that is associated with a low hygiene level and/or missing hygiene related events induces the closure of a barrier.

A Newborn Monitoring System

According to some embodiments of the present invention, the system 100 is used for monitoring newborns. Optionally, each newborn is tagged with a personal hygiene monitor 103 that is attached to one of her limbs, for example her hand. Optionally, the personal hygiene monitor 103 is also use as the newborn identification tag. In such an embodiment, the personal hygiene monitor 103 may be used for monitoring the newborn's caretaking. For example, the personal hygiene monitor 103 may be used for monitoring the feeding, washing, and changing of the newborn.

Additionally or alternatively, the personal hygiene monitor 103 is used for monitoring the location of the newborns in a certain area of interest. In such an embodiment, a system operator, a caretaker, and/or a mother may verify the hygiene level, feeding status and/or last changing event of a newborn in real time. In such an embodiment, the sensors of the personal hygiene monitor 103 are used for detecting and logging the hygiene level, feeding status and/or a changing event.

Additionally or alternatively, the personal hygiene monitors 103, or similar monitors, comprise a location detecting module, for example as depicted in 311, for identifying the location of the newborn. When the personal hygiene monitor 103 detects a personal hygiene event, it associates the event with the identified location of the user. Optionally, the personal hygiene monitor 103 records and optionally transmits the location of the newborn periodically, constantly, and/or randomly. Such a log can be used to determine whether, which, and to what extent, a personal hygiene event has occurred and where the newborn is located during his stay in the area of interest, which is optionally a maternity ward.

According to some embodiments of the present invention, a personal hygiene monitor 103, or a similar personal monitor, which are inserted in a bracelet or a watch, for example as shown at FIG. 3, is paired with another personal hygiene monitor 103, or similar personal monitor. Optionally, each one of the personal monitors includes a tag indicating its pairing relation to other personal monitors which have similar tags.

Such pairing allows matching patients are designated to share a medical treatment, a feeding session, a hygiene session and the like. For example, while one personal monitor is attached to a newborn, a pairing personal monitor is attached to his mother. Such pairing may be used for assuring that a newborn is released from a maternity ward only with her mother. Optionally, the system 100 includes one or more markers, such as the aforementioned hygiene markers 106, which are designed to detect the presence and/or the location of the personal monitors 103 in proximity thereto. The hygiene markers 106 notify a central unit, such as the aforementioned analysis unit 102, about the location of paired personal monitors. In such a manner, the analysis unit 102 may monitor the geometric or Euclidean distance between the paired personal monitors. Optionally, if the monitored distance exceeds a certain threshold, for example 50 meters, 20 meters, 10 meters, and or less, for example for a period of more that 30 seconds, the analysis unit 102 presents an alarm. Optionally, the personal monitors are designed to receive signals from the analysis unit 102, for example via one or more markers, such as the aforementioned hygiene markers 106. In such a manner, the monitor may sound and/or display an alarm if the monitored distance exceeds a certain threshold. In such a manner, the personal monitors may be used for preventing a scenario in which newborns mix-up occurs. Optionally, the analysis unit 102 is connected, optionally wirelessly, with one or more controllers which are connected to barriers, such as automatic doors and turnstiles in order to ensure sufficient control on the location of newborns. In such an embodiment the activation of one of the aforementioned alarms may lock barriers, such as automatic doors and turnstiles which are located in proximity to the personal monitors. Optionally, barriers are opened when a pair of matching personal monitors in detected, for example a personal monitor of a mother and her newborn. Additionally or alternatively, the barrier is locked if unmatched personal monitors are detected. In such an embodiment, the barrier is opened only if a mother tries to pass therethrough with her newborn and closed if the mother tries to pass therethrough with another newborn. Optionally, a personal monitor with a master tag that can be matched with any other personal monitor is given to selected caretakers, such as nurses and physicians.

System Management

In use, the system 100 may be used for analyzing a hygiene level of a plurality of users. As described above, the hygiene analysis unit 102 manages a plurality of user profiles 107 for a plurality of users which are attached to personal hygiene monitors 103. The communication terminals 105 allow each one of the personal hygiene monitors 103 to interface with the hygiene analysis unit 102. In such a manner, the user profiles 107 may be updated with the data that is logged in the memory units of the respective personal hygiene monitors 103.

Optionally, the system 100 is used for scoring the hygiene habits of a group of users. The hygiene level of each user is optionally a relative rank that is determined according to hygiene levels of other users. For example, the hygiene level of each user may be converted to a rank based on one hundred percent that is set as the sum of all the hygiene level values of all the users. In such an embodiment, the system 100 may manage a reward mechanism in which user are rewarded according to there relative score. For example, users in the highest percentile receive an addition to their salary and users in the lowest percentile are required to pay a penalty. In another embodiment, the reward mechanism publishes a list that ranks all the users according to their hygiene level. Such an embodiment may motivate the user to maintain a high level of hygiene habits in order to preserve and/or to improve her rank. Optionally, the MMI 307 is designed to present the user hygiene level and/or rank in a manner that is noticeable for other users and/or patients. For example, the MMI may change the color of the display, set an indicator LED to show a color that reflects the hygiene level and/or the rank and the like.

It is expected that during the life of a patent maturing from this application many relevant apparatuses, methods, and systems will be developed and the scope of the terms personal hygiene event and personal hygiene sensor is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for analyzing hygiene habits of a user, comprising:
   attaching a wearable personal hygiene monitor sized and shaped for being worn on a body organ of the user and for holding motion detection sensor to the user;
   using said motion detection of said attached wearable personal hygiene monitor for monitoring the motion of the wearable personal hygiene monitor and detecting a plurality of personal hygiene events related to the user;
   using said attached wearable personal hygiene monitor to estimate the quality of at least one of a plurality of personal hygiene events and calculate locally and accordingly a hygiene level of one or more hygiene habits of the user; and
   using said attached personal hygiene monitor to present an indication of said hygiene level on the body of the user;
   wherein said motion detection sensor comprises at least one of an accelerometer and a gyroscope.

2. The method of claim 1, further comprising presenting an alarm on said attached wearable personal hygiene monitor when said hygiene level being beyond a predefined level.

3. The method of claim 1, further comprising ranking the hygienic level of said user in relation to a plurality of users according to said hygiene level.

4. The method of claim 1, wherein said calculating is based on a schedule of the user.

5. The method of claim 1, further comprising logging said plurality of personal hygiene events and associating a time stamp with each said personal hygiene event, further comprising identifying at least one personal hygiene pattern according to respective said associated time stamps, said calculating being performed according to said at least one personal hygiene pattern.

6. The method of claim 1, wherein said using comprises using said attached wearable personal hygiene monitor for gathering locational data regarding the user, further comprising identifying at least one personal hygiene pattern according to a combination of said locational data and at least one of said plurality of personal hygiene events, said calculating being performed according to said at least one personal hygiene pattern.

7. The method of claim 1, wherein said personal hygiene event is a member of a group consisting of: using a disposable tissue, washing hand action, taking shower action, replacing medical safety accessory action, replacing a pair of gloves action, and wearing a face mask action.

8. The method of claim 1, wherein said detecting comprises detecting and logging the quality of said personal hygiene event, said calculating being performed according to respective qualities.

9. The method of claim 8, wherein said quality is estimated by measuring a member of a group consisting of: measuring the duration of said respective personal hygiene event, measuring the intensity of said respective personal hygiene event, measuring a concentration of at least one disinfecting agent involved in said personal hygiene event, measuring a presence of water during said personal hygiene event, measuring a humidity level during said personal hygiene event, measuring temperature during said personal hygiene event.

10. The method of claim 1, further comprising using said attached wearable personal hygiene monitor for monitoring presence of the user, said detecting comprising logging said presence and said calculating comprises estimating a hygiene level pattern based on a combination of said hygiene level and said presence.

11. The method of claim 1, further comprising using said attached wearable personal hygiene monitor for monitoring presence of the user, said calculating is performed according to said presence.

12. The method of claim 1, further comprising operating a barrier according to said hygiene level.

13. A wearable apparatus for analyzing hygiene habits of a user, comprising:

at least one sensor configured for detecting a plurality of personal hygiene events of the user;
a repository configured for storing said plurality of personal hygiene events; and
an analysis unit configured for estimating a hygiene level of at least one hygiene habit of the user according to said plurality of personal hygiene events;
a hygiene indicator configured for presenting said hygiene level to the user; and
a wearable element sized and shaped for being worn on a body organ of the user and for holding said at least one sensor, said repository, and said analysis unit, and said hygiene indicator in proximity to the body of the user;
wherein said analysis unit is configured for estimating a hygiene level of at least one hygiene habit of the user according to said plurality of personal hygiene events;
wherein said at least one sensor comprises a motion detection sensor which monitors the motion of the wearable apparatus to estimate the quality of at least one of said plurality of personal hygiene events;
wherein said motion detection sensor comprises at least one of an accelerometer and a gyroscope.

14. The wearable apparatus of claim 13, further comprising a wearing detector for detecting a wearing event of the wearable apparatus, wherein each said personal hygiene event is evaluated according to said wearing event.

15. The wearable apparatus of claim 13, wherein said at least one sensor comprises a plurality of sensors, each being configured for detecting a different of a plurality of physical stimulations, said at least one sensor being configured for detecting said plurality of personal hygiene events by combining said plurality of physical stimulations.

16. The wearable apparatus of claim 13, wherein said at least one sensor comprises a plurality of sensors, each being configured for detecting a different of a plurality of physical stimulations, said analysis unit being configured for estimating said hygiene level by combining said plurality of physical stimulations.

17. The wearable apparatus of claim 13, further comprising an interface configured for forwarding said plurality of personal hygiene events to a remote analysis unit; wherein said remote analysis unit maintaining a user hygiene profile documenting at least one hygiene habit related to the user, said remote analysis unit being configured for updating said user hygiene profile according to said plurality of personal hygiene events and calculating said hygiene level according to said user hygiene profile.

18. The wearable apparatus of claim 13, wherein said at least one sensor comprises an touch detector sensor configured for detecting a proximity of to a medical device and a processor configured for detecting a personal hygiene event according to said detected proximity.

19. The wearable apparatus of claim 13, wherein said at least one sensor comprises an touch detector sensor configured for detecting a touch event during which the user touching at least one of a medical device and a patient, said analysis unit configured for estimating said personal hygiene event according to said touch event.

20. The wearable apparatus of claim 13, wherein said at least one sensor is configured for detecting a hygiene protection event, said repository being configured for storing said hygiene protection event, and said analysis unit being configured for estimating said hygiene level according to said hygiene protection event.

21. The wearable apparatus of claim 13, further comprising a location detecting module configured for detecting a location of the user and logging it in said repository, said analysis unit being configured for estimating said hygiene level according to said location.

22. The wearable apparatus of claim 21, wherein said location is outside the boundaries of a building.

23. The wearable apparatus of claim 21, wherein said location is a member of a group consisting of: a include an operating room, a patient bed, a medical device, a physiotherapy room, a dining room, a kitchen, a production floor shop, food manufacturing area and a food manufacturing device.

24. The wearable apparatus of claim 13, wherein said at least one sensor comprises a proximity sensor that estimates the distance between the wearable apparatus and at least one of a tap or a disinfectant dispenser to detect at least one of said plurality of personal hygiene events.

25. A wearable apparatus for analyzing hygiene habits of a user, comprising:
at least one sensor configured for detecting a plurality of personal hygiene events of the user;
a repository configured for storing said plurality of personal hygiene events; and
an analysis unit configured for estimating a hygiene level of at least one hygiene habit of the user according to said plurality of personal hygiene events;
a hygiene indicator configured for presenting said hygiene level to the user; and
a wearable element sized and shaped for being worn on a body organ of the user and for holding said at least one sensor, said repository, and said analysis unit, and said hygiene indicator in proximity to the body of the user;
wherein said analysis unit is configured for estimating a hygiene level of at least one hygiene habit of the user according to said plurality of personal hygiene events;
wherein said at least one sensor comprises a hygrometer for detecting at least one of said plurality of personal hygiene events by measuring humidity in a proximity to the hands of the user.

26. A wearable apparatus for analyzing hygiene habits of a user, comprising:
at least one sensor configured for detecting a plurality of personal hygiene events of the user;
a repository configured for storing said plurality of personal hygiene events; and
an analysis unit configured for estimating a hygiene level of at least one hygiene habit of the user according to said plurality of personal hygiene events;
a hygiene indicator configured for presenting said hygiene level to the user; and
a wearable element sized and shaped for being worn on a body organ of the user and for holding said at least one sensor, said repository, and said analysis unit, and said hygiene indicator in proximity to the body of the user;
wherein said analysis unit is configured for estimating a hygiene level of at least one hygiene habit of the user according to said plurality of personal hygiene events;
wherein said at least one sensor comprises an alcohol sensor for detecting at least one of said plurality of personal hygiene events by measuring a concentration of alcohol vapours in a proximity to the user.

27. A wearable apparatus for analyzing hygiene habits of a user, comprising:
at least one sensor configured for detecting a plurality of personal hygiene events of the user;
a repository configured for storing said plurality of personal hygiene and an analysis unit configured for estimating a hygiene level of at least one hygiene habit of the user according to said plurality of personal hygiene events;

a hygiene indicator configured for presenting said h hygiene level to the user; and a wearable element sized and shaped for being worn on a body organ of the user and for holding said at least one sensor, said repository, and said analysis unit, and said hygiene indicator in proximity to the body of the user;

wherein said analysis unit is configured for estimating a hygiene level of at least one hygiene habit of the user according to said plurality of personal hygiene events;

wherein said at least one sensor comprises an ultrasonic Doppler sensor for detecting at least one of said plurality of personal hygiene events by detecting running water by means of measuring Doppler Effect in a proximity to the user.

28. A wearable apparatus for analyzing hygiene habits of a user, comprising:

at least one sensor configured for detecting a plurality of personal hygiene events of the user;

a repository configured for storing said plurality of personal hygiene events; and an analysis unit configured for estimating a hygiene level of at least one hygiene habit of the user according to said plurality of personal hygiene events;

a hygiene indicator configured for presenting said hygiene level to the user; and a wearable element sized and shaped for being worn on a body organ of the user and for holding said at least one sensor, said repository, and said analysis unit, and said hygiene indicator in proximity to the body of the user;

wherein said analysis unit is configured for estimating a hygiene level of at least one hygiene habit of the user according to said plurality of personal hygiene events;

wherein said at least one sensor comprises an optical sensor for detecting at least one of said plurality of personal hygiene events by measuring a transparency of cleaning material in a proximity to the user.

29. A wearable apparatus for analyzing hygiene habits of a user, comprising:

at least one sensor configured for detecting a plurality of personal hygiene events of the user;

a repository configured for storing said plurality of personal hygiene events; and an analysis unit configured for estimating a hygiene level of at least one hygiene habit of the user according to said plurality of personal hygiene events;

a hygiene indicator configured for presenting said hygiene level to the user; and a wearable element sized and shaped for being worn on a body organ of the user and for holding said at least one sensor, said repository, and said analysis unit, and said hygiene indicator in proximity to the body of the user;

wherein said analysis unit is configured for estimating a hygiene level of at least one hygiene habit of the user according to said plurality of personal hygiene events;

wherein said at least one sensor comprises an acoustical sensor for detecting the sound of personal hygiene events by comparing between acoustical signals captured in a proximity to the user and a predefined audio pattern.

30. A wearable apparatus for analyzing hygiene habits of a user, comprising:

at least one sensor configured for detecting a plurality of personal hygiene events of the user;

a repository configured for storing said plurality of personal hygiene events; and an analysis unit configured for estimating a hygiene level of at least one hygiene habit of the user according to said plurality of personal hygiene events;

a hygiene indicator configured for presenting said hygiene level to the user; and a wearable element sized and shaped for being worn on a body organ of the user and for holding said at least one sensor, said repository, and said analysis unit, and said hygiene indicator proximity to the body of the user;

wherein said analysis unit is configured for estimating a hygiene level of at least one hygiene habit of the user according to said plurality of personal hygiene events;

wherein said at least one sensor comprises a motion detection sensor for detecting a personal hygiene event by recording at least one gesture of said user and matching between said at least one gesture and at least one movement pattern of a personal hygiene event.

31. A system for analyzing hygiene habits of a plurality of users, comprising:

a plurality of wearable personal hygiene monitors each sized and shaped for being worn on a body organ of a respective of the plurality of users and comprises a motion detection sensor which monitors the motion of the wearable apparatus to allow detecting and locally logging a plurality of wearable personal hygiene events related thereto and to estimate the quality of at least one of said plurality of wearable personal hygiene events; and a hygiene analysis unit configured for managing a plurality of user hygiene profiles each documenting at least one hygiene habit of a respective of the plurality of users, said hygiene analysis unit being configured for receiving the quality of at least one of said plurality of wearable personal hygiene events from a respective of said plurality of wearable personal hygiene monitors and updating a respective of said plurality of user hygiene profile accordingly;

wherein said hygiene analysis unit is configured for calculating a hygiene level for each said user according to a respective of said plurality of user hygiene profiles;

wherein said motion detection sensor comprises at least one of an accelerometer and a gyroscope.

32. The system of claim 31, further comprising a plurality of location detecting unit each configured for detecting the presence of at least one of said plurality of wearable personal hygiene monitors in proximity thereto, wherein said hygiene analysis unit is configured for calculating said hygiene level according to detected presence.

33. A wearable apparatus for analyzing hygiene habits of a user, comprising:

at least one sensor configured for detecting a plurality of personal hygiene events of the user;

a repository configured for storing said plurality of personal hygiene events; and an analysis unit configured for estimating a hygiene level of at least one hygiene habit of the user according to said plurality of personal hygiene events;

a hygiene indicator configured for presenting said hygiene level to the user; and a wearable element sized and shaped for being worn on a body organ of the user d for holding said at least one sensor, said repository, and said analysis unit, and said hygiene indicator in proximity to the body of the user;

wherein said analysis unit is configured for estimating a hygiene level of at least one hygiene habit of the user according to said plurality of personal hygiene events;

wherein said at least one sensor comprises a electromagnetic sensor that measures an alternating magnetic field of running water and determines a quality of at least one of said plurality of personal hygiene events accordingly.

\* \* \* \* \*